United States Patent [19]

Illum

[11] Patent Number: 5,629,011
[45] Date of Patent: May 13, 1997

[54] COMPOSITION FOR NASAL ADMINISTRATION

[75] Inventor: Lisbeth Illum, Nottingham, United Kingdom

[73] Assignee: Danbiosyst UK Limited, Nottingham, United Kingdom

[21] Appl. No.: 256,431

[22] PCT Filed: Feb. 4, 1993

[86] PCT No.: PCT/GB93/00228

§ 371 Date: Jul. 12, 1994

§ 102(e) Date: Jul. 12, 1994

[87] PCT Pub. No.: WO93/15737

PCT Pub. Date: Aug. 19, 1993

[30] Foreign Application Priority Data

Feb. 5, 1992 [GB] United Kingdom ............... 9202464

[51] Int. Cl.$^6$ ........................................ A61K 9/50
[52] U.S. Cl. ........................ 424/434; 424/489; 424/499
[58] Field of Search ........................... 424/434, 489, 424/499

[56] References Cited

U.S. PATENT DOCUMENTS

5,362,498  11/1994  Aiache ........................... 424/435

FOREIGN PATENT DOCUMENTS

0205282  12/1986  European Pat. Off. .
3602370  8/1987  Germany .
8203768  11/1982  WIPO .

OTHER PUBLICATIONS

Brown et al., "Analgesic Potencies of Morphine-3-and 6-Sulfates . . .," *J. Pharm. Sci*, vol. 74, No. 8, Aug. 1985, pp. 821–824.

Osbourne et al., "Analgesic Activity of Morphine-6-Glucuronide," *Lancet*, Apr. 6, 1988, p. 828.

Houdi et al., "Potent Central Activity of Morphine . . .," *Pharm. Res.* 9, 5–103 (1992).

Hanna et al, "Disposition of Morphine-6-. . .," *British J. Anaesthesia*, 66:pp. 103–107; (1991).

Rally, "Intranasal Opiates . . .," *Can. J. Anaesth.*, vol. 36, No. 5, pp. 491–493 (1989).

Pasternak et al, "Morphine-6-Glucuronide . . .," *Life Sciences*, vol. 41, No. 2845 (1987).

*Primary Examiner*—Jyothsna Venkat
*Attorney, Agent, or Firm*—Arnall Golden & Gregory

[57] ABSTRACT

A composition for nasal administration of polar metabolites of opioid analgesics comprises a polar metabolite of an opioid analgesic and an absorption promoting agent. Preferred metabolites morphine-6-glucuronide and morphine-6-sulphate. A preferred absorption promoting agent is chitosan but other suitable agents include cationic polymers, bioadhesive agents, surface active agents, fatty acids, chelating agents, mucolytic agents, cyclodextrin, microsphere preparations or combinations thereof.

22 Claims, No Drawings

COMPOSITION FOR NASAL ADMINISTRATION

This invention relates to a composition for nasal administration and more particularly to a composition for the nasal administration of the polar metabolites of opioid analgesics.

Opioid analgesics have a useful role in pain relief, particularly for patients in the terminal stages of cancer. Morphine is a widely used agent and can be administered via injection as an oral controlled release formulation or by suppository. Morphine has also been given via the nasal route and morphine snuff was described in the last century.

The intranasal administration of opiates has been discussed by Ralley (Can. J. Anaesth. 36, 5 491 . 493 (1989) who suggested that morphine could be given by this route. The route was relatively free of side effects normally associated with opioids but a possible disadvantage was the short duration of sedation which lasted only up to 60 minutes.

Nasal administration of morphine is discussed in EP 205282 where a sustained release effect is achieved through the use of a cellulosic derivative that adheres to the mucosa. A solid unit dosage form is described.

WO 8203768 describes a system for nasal drug delivery comprising morphine or its analogues having at least one phenolic hydroxy group with a non toxic nasal carrier. Ointments, gel solution or suspension salts of morphine are preferably used in the sustained release products.

It is well known that the therapeutic use of morphine gives rise to various side effects, including constipation and respiratory depression. Recently it has been disclosed that some of the metabolites of morphine, namely morphine-6-glucuronide and morphine-6-sulphate may be several times more active than the parent drug and is less likely to have the unwanted side effects (Pasternak et al (1987) Life Sciences 41, 2845; Hanna et al. (1991) Brit. J. Anaes. 66, 103; Brown et al (1985) J Pharm. Sci. 74,821). They may also have a longer biological half-life. The use of morphine-6-glucuronide as a drug substance in its own right has been discussed in the pharmaceutical and medical literature (Osborne et al (1988) Lancet April 6 p.828). Similarly, morphine-6-sulphate has been described in the literature as an analgesic agent (Brown et al Supra). However, the major problem facing delivery of these agents and polar metabolites of this and other opioid analgesics by methods other than injection, is the high water solubility of the compounds. It is unlikely that the materials will be well absorbed across mucosal surfaces, for example from the gastrointestinal tract. It is possible that the glucuronides would be absorbed from the colon but this would only occur after the glucuronide was converted back to the parent compound by the action of the reducing conditions within the large bowel created by the microbial flora in that region. The polar nature of the compounds also means that they are likely to be poorly transported across normal mucosal surfaces such as the nasal, buccal, vaginal and rectal mucosae. However, we have now found, surprisingly, that the absorption of such polar metabolites across the nasal mucosa can be greatly increased by combination with an absorption promoting agent.

Thus the present invention provides a composition for nasal administration comprising a polar metabolite of an opioid analgesic and an absorption promoting agent. A preferred metabolite is a glucuronide, especially morphine-6-glucuronide, however glucuronides of other opioid analgesics such as codeine, levorphanol, hydromorphone, oxymorphone, nalbuphine, buprenorphine, nalorphine, hydrocodone, oxycodone and butorphanol are also suitable.

A further preferred metabolite is a sulphate, especially morphine-6-sulphate but again sulphates of other opioid analgesics such as those mentioned above are also suitable.

Opioid analgesics are metabolised in the body to a variety of compounds that are more polar than morphine itself, and this is what we mean by the term metabolite as used herein. The polar nature of a compound can be determined by measuring its partition coefficient between an aqueous buffer and an organic solvent such as octanol. The partition coefficient of morphine, expressed as a logarithm (logP) partitioned between an aqueous buffer and octanol ranges from 0.70 to 1.03 (Hansch C. and Leo A. "Substituent Constants for Correlation Analysis in Chemistry and Biology" Wiley, N.Y., 1979). The polar metabolites of morphine will therefore have a lower logP value than that of morphine. The major metabolites of morphine are morphine-3-glucuronide (M3G) and morphine-6-glucuronide (M-6G). Formation of the ethereal sulphates at positions 3 and 6 in the molecule may also occur. Morphine-6-sulphate which differs from morphine itself by having an ionizable group of Carbon-6 at physiological pH has been shown to be a more potent analgesic than morphine following intracerebroventricular administration in mice (Brown et al (1985) J. Pharm. Sci. 74 821). Morphine-6-sulphate and a number of its 3-O-acetyl derivatives exhibit potent antinociceptive activity in the rat when given by subcutaneous injection (Houdi, et al (1992) Pharm. Res. 9 S-103).

The structures of morphine-6-glucuronide and morphine-6-sulphate are shown below:

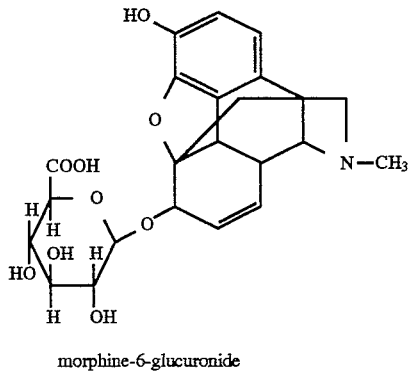

morphine-6-glucuronide

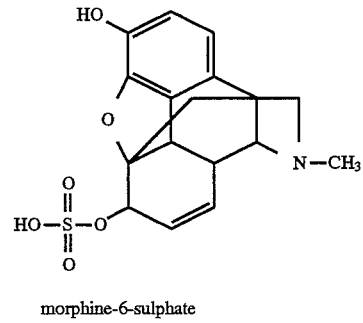

morphine-6-sulphate

The absorption promoting agent should be such that it provides therapeutic levels of metabolite in the plasma with an absorption efficiency of greater than 10% and preferably greater than 30%. The absorption is measured in terms of the bioavailability, which is defined as the ratio of the quantity of metabolite appearing in the blood after intranasal administration compared to that found after intravenous administration, expressed as a percentage.

The therapeutic level of the metabolite achieved should be a plasma concentration that is at least as equipotent as the level required for the opioid analgesic for analgesic effect. For morphine, the usual therapeutic levels in plasma are from 1–500 ng/ml, and more typically 20–100 ng/ml. Data have indicated that, for example, morphine-6-glucuronide and morphine-6-sulphate could be many times more active than morphine. Thus the required therapeutic levels of morphine-6-glucuronide and morphine6-sulphate may be in the same range as those for morphine or they may be much lower and it is the potency that will decide the required concentration. Although more work is required in this area, morphine-6-glucuronide and morphine6-sulphate levels may be expected to be in the region of two times less than those of morphine to give the same pain relief effect.

The composition of the invention may be used for pain relief in a variety of situations but especially to relieve chronic pain in terminal cancer patients, for acute pain, for example after dental surgery and for other post-operative pain.

The absorption promoting agent is desirably a cationic polymer, a bioadhesive agent, a surface active agent, a fatty acid, a chelating agent, a mucolytic agent, a cyclodextrin or combinations thereof or a microsphere preparation, and may be present in the composition as a solution in an aqueous medium, a dispersion in an aqueous medium, as a powder or as microspheres. The terms used here are not intended to be mutually exclusive.

Chitosan, a cationic polymer, is a preferred absorption enhancer. Chitosan is deacetylated chitin, or poly-N-acetyl-D-glucosamine. It is available from Protan Laboratories Inc, Redmond, Wash. 98052, U.S.A. and, depending on the grade selected, can be soluble in water up to pH 6.0. A 1% solution of non-water soluble chitosan (Sea Cure) may be made by making a slurry (eg 2 g/100 ml) in water and adding an equal volume of organic acid (eg 100 ml of 2% acetic acid) and stirring vigorously for one hour. Water-soluble chitosan (Sea Cure$^+$) may dissolve without organic or inorganic acids being present. The chitosan may also be used as chitosan microspheres.

Chitosan has previously been used to precipitate proteinaceous material, to make surgical sutures and as an immunostimulant. It has also been employed previously in oral drug formulations in order to improve the dissolution of poorly soluble drugs (Sawayanagi et al, (1983) Chem. Pharm. Bull., 31, 2062–2068) or for the sustained release of drugs (Nagai et al, Proc. Jt. US- Jpn. Semin. Adv. Chitin, Chitosan, Relat. Enzymes, 21–39. Zikakis J. P. (ed), Academic Press. Orlando (1984)) by a process of slow erosion from a hydrated compressed matrix.

Diethylaminoethyl-dextran (DEAE-dextran) is also suitable and is a polycationic derivative of dextran containing diethylaminoethyl groups coupled to the glucose residues by ether linkages. The parent dextran can have an average molecular weight of about 5,000 to $40\times10^6$, but is typically about 500,000.

Further cationic polymers which may be used in the compositions of the invention include other polycationic carbohydrates such as but not limited to inorganic or organic salts of chitosan and modified forms of chitosan (especially more positively charged ones), polyaminoacids such as polylysine, polyquaternary compounds, protamine, polyamine, DEAE-imine, polyvinylpyridine, polythiodiethyl-aminomethylethylene (P(TDAE)), polyhistidine, DEAE-methacrylate, DEAE-acrylamide, poly-p-aminostyrene, polyoxethane, co-polymethacrylates (e.g. copolymers of HPMA, N-(2-hydroxypropyl)-methacrylamide, GAFQUAT (U.S. Pat. No. 3,910,862) and polyamidoamines. The polycationic substances used in the invention typically have a molecular weight of 10 000 or more. The chitosan (or salt thereof) preferably has an intrinsic viscosity of at least 400 ml/g, more preferably at least 500, 750 or 1000 ml/g.

The concentration of the cationic polymer in a solution is preferably 0.01 to 50% w/v, more preferably 0.1 to 50% and more preferably 0.2 to 30%.

Amongst the bioadhesive agents suitable for use are included bioadhesive microspheres. Preferably the microspheres are prepared from a bio-compatible material that will gel in contact with the mucosal surface. Substantially uniform solid microspheres are preferred. Starch microspheres (crosslinked if necessary) are a preferred material. Other materials that can be used to form microspheres include starch derivatives, modified starches such as amylodextrin, gelatin, albumin, collagen, dextran and dextran derivatives, polyvinyl alcohol, polylactide-co-glycolide, hyaluronic acid and derivatives thereof such as benzyl and ethyl esters, gellan gum and derivatives thereof such as benzyl and ethyl esters and pectin and derivatives thereof such as benzyl and ethyl esters. By the term "derivatives" we particularly mean esters and ethers of the parent compound that can be unfunctionalised or functionalised to contain, for example, ionic groupings.

Suitable starch derivatives include hydroxyethyl starch, hydroxypropyl starch, carboxymethyl starch, cationic starch, acetylated starch, phosphorylated starch, succinate derivatives of starch and grafted starches. Such starch derivatives are well known and described in the art (for example Modified Starches: Properties and Uses, O. B. Wurzburg, CRC Press Boca Raton (1986)).

Suitable dextran derivatives include, diethylaminoethyl-dextran (DEAE-dextran), dextran sulphate, dextran methyl-benzylamide sulphonates, dextran methyl-benzylamide carboxylates, carboxymethyl dextran, diphosphonate dextran, dextran hydrazide, palmitoyldextran and dextran phosphate.

Preparation of these microspheres is well described in the pharmaceutical literature (see for example Davis et al., (Eds), "*Microspheres and Drug Therapy*", Elsevier Biomedical Press, 1984, which is incorporated herein by reference). Emulsion and phase separation methods are both suitable. For example, albumin microspheres may be made using the water-in-oil emulsification method where a dispersion of albumin is produced in a suitable oil by homogenization techniques or stirring techniques, with the addition if necessary of small amounts of an appropriate surface active agent. The size of the microspheres is largely dictated by the speed of stirring or homogenization conditions. The agitation can be provided by a simple laboratory stirrer or by more sophisticated devices such as a microfluidizer or homogenizer. Emulsification techniques are also used to produce starch microspheres as described in GB 1 518 121 and EP 223 303 as well as for the preparation of microspheres of gelatin. Proteinaceous microspheres may also be prepared by coacervation methods such as simple or complex coacervation or by phase separation techniques using an appropriate solvent or electrolyte solution. Full details of the methods of preparing these systems can be obtained from standard text books (see for example Florence and Attwood, *Physicochemical Principles of Pharmacy* 2nd Ed., MacMillan Press, 1988, Chapter 8).

For example, microspheres were prepared as follows:
The preparation of starch microspheres using emulsification A 10% starch gel was prepared by heating (70° C.) 5 g of starch with 40 ml of water until a clear gel was formed. After cooling water was added to a volume of 50 ml. 20 ml of the starch gel was added to 100 ml of soya oil containing antioxidant and 1% v/v Span 80 and homogenised at 7000 rpm for 3 minutes. This emulsion was added to 100 ml hot (80° C.) soya oil BP (containing antioxidant) and stirred at 1500 rpm while heated to 115° C. over 15 minutes. The emulsion was left stirring at 115° C. for 15 minutes and then rapidly cooled. 100 ml of acetone was added and the microspheres were centrifuged at 4500 rpm for 15 minutes. They were then washed with acetone and air dried. The microspheres can be separated into the desired size fraction (for example 1–10 µm) using appropriate sieves.

Preparation of hyaluronic acid ester microspheres by solvent extraction

An emulsion was formed by mixing a 6% w/v solution of the polymer eg benzyl hyaluronic acid ester (Hyaff-11) in dimethylsulphoxide with white mineral oil containing 0.5% Arlacel A. The inner phase was added to the outer oil phase (their respective ratio being 1:16 v/v) with continuous stirring for 10 minutes. (1000 rpm). Ethyl acetate, the extraction solvent, was then added to the emulsion at a ratio of 2:1 v/v. The extraction proceeded for 15 minutes at a stirring rate of 700 rpm until the microparticles were formed. The microsphere suspension was filtered and extensively washed with n-hexane and dried. Drug can be incorporated into the microspheres by addition to the initial polymer solution.

The obtained microsphere size was 2–10 µm.

The preparation of albumin microspheres using an emulsification technique and heat stabilisation 100 ml Soya oil was mixed with 1 ml of a 10% albumin solution and homogenised at 6000 rpm. The emulsion was added to 200 ml soya oil at 50° C. and stirred at 1500 rpm. The emulsion was heated to 120° C. and equilibrated for 20° C. at this temperature. The microspheres were cooled to room temperature and washed with petroleum ether, followed by ethanol and acetone. They were then filtered and dried. Microspheres of 1–10 µm were obtained.

Preparation of Albumin microspheres using a coacervation technique 10 ml 25% HSA solution (ph=5) was stirred (500rpm) while a 30% solution of PEG was added (2.5 ml) until phase separation occurred. The system was stirred for 15 minutes before the albumin droplets was solidified by slowly heating the mixture to 90° C. and keeping it at this temperature for 30 minutes. Instead of heat denaturation, glutaraldehyde can be used to crosslink the albumin but this latter method seems to make the particles aggregate to a greater extent than that seen with the heat denaturation. The microspheres were then isolated by filtration and freeze dried.

With a stirring speed of 500 rpm particles with a mean size of 43 µm±6 µm was produced.

Preparation of soluble potato starch microspheres using a coacervation technique 15 ml 5% starch solution (pH=7) was kept at a constant temperature of 70° C. and stirred (500 rpm) while a 30% solution of PEG was added (7 ml) until phase separation had occurred, the system was stirred for further 15 minutes before it was cooled on ice during constant stirring. The microspheres were then isolated by filtration and freeze dried.

With a stirring speed of 500 rpm particles with a mean size of 33 µm±10 µm was produced.

Preparation of gelatine microspheres using a coacervation technique 30 ml 10% bovin gelatine (pH=8.5) was kept at a constant temperature of 50° C. and stirred (500 rpm) while a 30% solution of PEG was added (20 ml) until the coacervation region was reached. To control this step a nephelometer can be used. The mixture was cooled on ice during constant stirring. The microspheres were isolated by filtration and freeze dried.

With a stirring speed of 500 rpm particles with a mean size of 60 µm±10 µm was produced.

Preparation of albumin microspheres using an emulsion technique 100 ml olive oil was mixed with 0.5–2 ml 25% HSA solution and the mixture was stirred for 15 minutes at 500–1000 rpm to form a w/o-emulsion. Solidification of the albumin droplets can be done either by the addition of 0.1–0.4 ml 25% glutaraldehyde and letting this react with the albumin for 15 minutes, or by heating the system to 90° C. for 30 minutes. In either case the microspheres are isolated by filtration, washed and freeze dried.

A stirring speed of 700 rpm gives a mean particle size of 53 µm±11 µm.

Preparation of gelatine microspheres using an emulsion technique 100 ml olive oil (70° C.) was mixed with 10 ml 5–10% gelatine solution and the mixture was stirred at 500–1500 rpm keeping the temperature constant at 70° C., the emulsion is stirred for 15 minutes and was then cooled on ice during constant stirring. The microspheres were isolated by filtration, washed and freeze dried.

A concentration of 10% gelatine and a stirring speed of 1000 rpm gives a mean particle size of 70 µm±8 µm.

Preparation of Chitosan microspheres

Chitosan microspheres were prepared by an emulsion technique as follows:

Chitosan, as for example a glutamate salt (70% degree of deacetylation), was dissolved in water to a concentration of 5% w/v. 100 ml soybean oil was mixed with 10 ml of the 5% Chitosan solution to form a water in oil emulsion. The microspheres were stabilized by adding dropwise 0.1 ml of a 25% w/v glutaraldehyde solution under continual stirring for 15 minutes. The microspheres were isolated by centrifugation, washed and freeze-dried. The size of the microspheres was in the range of 10–90 µm.

The microspheres obtained may be sieved if necessary in order to separate out microspheres in a desired size range. Other size separation techniques (air elutriation) may also be employed. The final microspheres can be modified by chemical cross-linking or heat treatment. Suitable cross-linking agents for use with starch microspheres include epichlorohydrin, terephthaloyl chloride and sodium trimetaphosphate. Suitable agents for use with albumin microspheres include aldehydes such as formaldehyde and glutaraldehyde, oxidised dextran ("dextranox") and 2,3-butanediose, the latter also being suitable for use with gelatin microspheres. Agents such as $N,N,N^1,N^1$-tetramethylethylenediamine can be used with dextran microspheres. The morphine metabolite can be incorporated into the microspheres during their preparation or sorbed into/onto the system after preparation. The effectiveness of the system can be controlled by the physical nature of the microsphere matrix and, for example, the extent of cross linking.

As an added advantage the particles may have variable controlled release characteristics through modifications made to the microsphere system, for example by controlling the degree of cross-linking or by the incorporation of excipients that alter the diffusional properties of the administered drug or by using mechanisms based on ion-exchange for metabolites that are ionizable in aqueous environments. For example DEAE-dextran and chitosan are positively charged and can be used for an ion-exchange interaction with metabolites that are negatively charged. The amount of drug that can be carried by the microspheres is termed the loading capacity, which is determined by the physicochemical properties of the drug molecule and in particular its size and affinity for the particle matrix.

Higher loading capacities are to be expected when the administered drug is incorporated into the microspheres during the actual process of microsphere manufacture. Microcapsules of a similar size, which are bioadhesive and which have controlled release properties, or any microcapsule which provide similar absorption promoting effects may also provide similar benefit as an absorption promoting agent. These microcapsules can be produced by a variety of methods. The surface of the capsule can be adhesive in its own right or can be modified by coating methods familiar to those skilled in the art. These coating materials are preferably bioadhesive polymers such as polycarbophil, carbopol, DEAE-dextran, alginates, or chitosan. Other bioadhesive powdery materials such as microcrystalline cellulose, dextrans and polycarbophils may also be used.

Surface active agents which are suitable include bile salts such as sodium deoxycholate and cholylsarcosine (a synthetic N-acyl conjugate of cholic acid with sarcosine [N-methylglycine]), and derivatives such as sodium tauro dihydrofusidate, non-ionic surfactants, such as laureth-9 (polyoxyethylene-9 lauryl ether), phospholipids and lysophosphatidyl compounds such as lysolecithin, lysophosphatidyl-ethanolamine, lysophosphatidylcholine, lysophosphatidylglycerol, lysophosphatidylserine, lysophosphatidic acid etc. Other phospholipid compounds soluble in water can be expected to demonstrate similar effects, for example short chain phosphatidylglycerol and phosphatidylcholines. A suitable concentration is from 0.02 to 10%. Phospholipids and lysophosphatides are preferred absoprtion promoting materials. Lysophosphatides are produced by the hydrolysis of phospholipids. Such materials are surface active and form micellar structures.

Lysophosphatidylcholine, which is produced from egg or soy lecithin, changes the permeability of membranes and allows the increased uptake of proteins and peptides including, for example, insulin, human growth hormone and other products of biotechnology and recombinant DNA methodologies. After administration the lysophosphatides are converted by the cells of the endothelial lining of the mucosa to the intact phosphatides which are normal cell components. (Lysolecithin itself is also present in cell membranes in very small quantities.) This rapid and efficient conversion of lysophosphatides into the complete phosphatide structure leads to much reduced adverse reactions and side effects in terms of irritation and toxicity.

Other lysophosphatidylcholines that have different acyl groups as well as lyso compounds produced from phosphatidylethanolamines, phosphatidylglycerols and phosphatidic acid which have similar membrane modifying properties may be used. Water soluble phospholipids with short acyl chains will also be appropriate since these are surface active. Acyl carnitines (e.g. palmitoyl-DL carnitinechloride) are an alternative. Other materials include acylcarnitines, acyl glycerols, non-ionic surfactants, fatty acids and salts (see for example list in Wearly, Crit. Rev. The. Drug Carrier Systems, 8:331–394 (1991), Table 2), glycyrrhetinates and biological detergents listed in the SIGMA catalog, 1988, page 316–321. Also agents that modify the membrane fluidity and permeability would be appropriate such as enamines (e.g phenylalanine enamine of ethyl-lacetoacetate), malonates, (e.g. diethyl-eneoxymethylene malonate), salicylates, bile salts and analogues and fusidates. Suitable concentrations would be up to 10%.

Examples of suitable chelating agents are EGTA, EDTA and alginates. Suitable mucolytic agents include thiol-containing compounds such as N-acetylcysteine and tyloxapol. Examples of suitable cyclodextrins are α-cyclodextrin, dimethyl-β-cyclodextrin, β-cyclodextrin, hydroxypopyl-β-cyclodextrin, γ-cyclodextrin, and 2-hydroxypropyl-β-cyclodextrin. Suitable peptide inhibitors include actinonin, amastatin, antipain, bestatin, chloroacetyl-HO-Leu-Ala-Glyn-NH$_2$, diprotinin A and B, ebelactone A and B, E-64, leupeptin, pepstatin A, phosphoramidon, H-Thr-(tBu)-Phe-Pro-OH, aprotinin, kallikrein, chymostatin, bensamidine, chymotrypsin, trypsin. Suitable concentrations would be from 0.01 to 5%.

For morphine-6-sulphate it is also possible to use structures complementary in charge and size that will complex with the molecule and thereby facilitate uptake across the nasal mucosa. Examples of suitable agents are betaines, alkyl alpha picolinium bromides, amino acids such as arginine and homoarginine hydrochlorides, labile quarternary ammonium salts, for example as described in U.S. Pat. No. 4,140,796, ion-pairing agents for anionic drugs for example those described by Jonkman and Hunt, (1983) Pharm Weekblad. Sci. Ed. 5 41 and N,N,dialkylpropionamides.

Preferred absorption promoting agents for use with both morphine-6-sulphate and morphine-6-glucuronide are bioadhesive microspheres, especially starch microspheres, or a lysophospholipid such as lysophosphatidylglycerol. Further preferred materials for use with morphine-6-glucuronide are chitosan and chelating agents such as EDTA.

Compositions according to the invention can be administered by any appropriate method according to their form. A composition comprising microspheres or a powder can be administered using a nasal insufflator device. Example of these are already employed for commercial powder systems intended for nasal application (e.g. Fisons Lomudal System).

The insufflator produces a finely divided cloud of the dry powder or microspheres. The insufflator is preferably provided with means to ensure administration of a substantially fixed amount of the composition. The powder or microspheres may be used directly with an insufflator which is provided with a bottle or container for the powder or microspheres. Alternatively the powder or microspheres may be filled into a capsule such as a gelatin capsule, or other single dose device adapted for nasal administration. The insufflator preferably has means to break open the capsule or other device.

A composition comprising a solution or dispersion in an aqueous medium can be administered as a spray using an appropriate device such as a metered dose aerosol valve or a metered dose pump. A gas or liquid propellant can be used. Details of other devices can be found in the pharmaceutical literature (see for example Bell, A. Intranasal Delivery Devices, in Drug Delivery Devices Fundamentals and Applications, Tyle P. (ed), Dekker, New York, 1988), Remington's Pharmaceutical Sciences, Mack Publishing Co., 1975.

The invention will now be further demonstrated with reference to the following example.

EXAMPLE 1

Experimental details

Morphine 6-glucuronide purchased from Ultrafine Chemicals, Salford, UK, was mixed in solution with the polycationic material chitosan, obtained from Protan Ltd of medium viscosity grade. The dose of morphine-6-glucuronide was 0.15 mg/kg. The chitosan concentration was 0.5%. The solution was administered into the sheep nostril using a simple spray pump device followed by serial blood sampling. The appearance of the morphine-6-glucuronide in the plasma was followed by taking serial blood samples, removing the red cells then assaying plasma samples for morphine 6-glucuronide. Control experiments were conducted using i.v. dosage of the glucuronide.

Dosing

Three animals (labelled NF, OF, PF) were given morphine-6-glucuronide intravenously as a bolus of 0.015 mg/kg and a further three animals (labelled IF, JF, KF) received nasally administered morphine-6-glucuronide at a dose of 0.15 mg/kg. Blood samples (10 ml) were taken at the following times.

Predose, 2, 5, 10, 15, 20, 30, 45, 60, 90, 120, 150, 180, 240, 300, 360 minutes.

Plasma was separated by centrifugation soon after sampling and the plasma samples (approximately 5 ml) were stored at −80° C. prior to analysis.

Assay for morphine–6-glucuronide in plasma

Plasma concentrations of morphine-6-glucuronide were determined by an improved method based on the published procedure of Svennson et al (1982) J. Chromatog. Biomed. Appl. 230, 427. The method involves solid phase extraction of morphine-6-glucuronide from the plasma sample followed by high-performance liquid chromatography analysis using electrochemical detection. The limit of quantification of the method is 1 ng/ml for a 0.5 ml plasma sample and the assay is linear over the range of 1 to 1200 ng/ml drug concentration.

During the period of analysis a seven point plasma standard calibration line (1 to 240 ng/ml) was routinely run on each day. Quality control samples consisting of sheep blank plasma spiked with known amounts of morphine-6-glucuronide were prepared in advance and stored at −20° C. These were analysed with the study samples on each day.

Calculation of plasma concentration

Plasma morphine-6-glucuronide concentrations were calculated by interpolation from a calibration line equation fitted by linear regression analysis. Morphine-6-glucuronide plasma concentrations of less than 1 ng/ml were regarded as not quantifiable within the limit of precision and accuracy of the assay.

Pharmacokinetic calculations

The plasma concentration of morphine-6-glucuronide versus time after administration of the four formulations was characterised in terms of the maximum observed concentration (Cmax), the time at which Cmax occurred (Tmax). The area under the curve (AUC) was calculated over 0–300 minutes using the linear trapezoidal method. The AUC values for the intravenous administration were normalised to the 0.15 mg/kg nasal dose for the calculation of bioavailability. The validity of this normalisation assumes linear kinetics for morphine-6-glucuronide up to a 0.15 mg/kg intravenous dose. Clearance was calculated by dividing the dose by the AUC, and the volume of distribution was calculated by dividing the clearance by the elimination rate constant. The bioavailability was calculated by dividing the mean AUC for nasal administration by the normalised mean AUC after intravenous administration.

Results

Plasma-concentration time data

The plasma concentrations of morphine-6-glucuronide in the plasma samples resulting from the intravenous and nasal doses are reported in Tables 1 and 2 respectively.

No morphine was detected in any of the plasma samples (limit of detection 1 ng/ml).

Pharmacokinetic analysis

The pharmacokinetic parameters calculated from the plasma concentration data after intravenous and nasal doses are shown in Tables 3 and 4 respectively.

Bioavailability

The mean nasal bioavailability was calculated to be 32.3% (n=3).

TABLE 1

PLASMA CONCENTRATIONS AFTER INTRAVENOUS ADMINISTRATION morphine-6-glucuronide concentration (ng/ml)

| Time (min) | SHEEP NF | SHEEP OF | SHEEP PF |
| --- | --- | --- | --- |
| Predose | nd | nd | nd |
| 2 | 43.8 | 37.9 | 49.5 |
| 5 | 40.3 | 54.7 | 34.6 |
| 10 | 36.1 | 47.0 | 31.8 |
| 15 | 28.6 | 37.3 | 28.5 |
| 20 | 23.2 | 41.7 | 29.8 |
| 30 | 22.5 | 32.1 | 24.3 |
| 45 | 13.4 | 30.3 | 20.0 |
| 60 | 12.0 | 25.0 | 14.7 |
| 90 | 9.4 | 17.7 | 11.6 |
| 120 | 5.6 | 12.6 | 8.6 |
| 150 | 3.5 | 7.3 | 3.5 |
| 180 | 2.0 | 3.8 | 1.9 |
| 240 | nd | 1.8 | 1.4 |
| 300 | nd | nd | nd |
| 360 | nd | nd | nd |

TABLE 2

PLASMA CONCENTRATIONS AFTER NASAL ADMINISTRATION morphine-6-glucuronide concentration (ng/ml)

| Time (min) | SHEEP IF | SHEEP JF | SHEEP KF |
| --- | --- | --- | --- |
| Predose | nd | nd | nd |
| 2 | nd | 13.3 | 17.1 |
| 5 | 21.8 | 50.5 | 65.3 |
| 10 | 89.1 | 165.3 | 109.3 |
| 15 | 121.4 | 154.8 | 110.3 |
| 20 | 101.9 | 122.5 | 94.9 |
| 30 | 107.2 | 105.5 | 80.9 |
| 45 | 108.5 | 83.6 | 73.5 |
| 60 | 66.7 | 64.9 | 45.7 |
| 90 | 41.1 | 41.3 | 29.3 |
| 120 | 21.9 | 29.2 | 19.1 |
| 150 | 16.0 | 25.9 | 12.7 |
| 180 | 10.2 | 10.0 | 6.3 |
| 240 | 2.7 | 6.9 | 3.0 |
| 300 | nd | 2.9 | nd |
| 360 | nd | nd | nd | nd = not detectable (less than 1.0 ng/ml)

TABLE 3

Pharmacokinetic parameters for morphine-6-glucuronide after intravenous administration to sheep

| Sheep Identity | Cmax (ng ml$^{-1}$) | Tmax (min) | T½ (min) | Area Under Curve (ng min ml$^{-1}$) | Clearance (ml min$^{-1}$ kg$^{-1}$) | Apparent Volume of Distibution (lkg$^{-1}$) |
| --- | --- | --- | --- | --- | --- | --- |
| NF | 44 | 2 | 58 | 2165 | 6.9 | 0.58 |
| OF | 55 | 5 | 53 | 3819 | 3.9 | 0.30 |
| PF | 50 | 2 | 42 | 2560 | 5.9 | 0.35 |
| Mean | 50 | 3 | 51 | 2848 | 5.6 | 0.41 |

TABLE 4

Pharmacokinetic parameters for morphine-6-glucuronide after nasal administration to sheep

| Sheep Identity | Cmax (ng ml$^{-1}$) | Tmax (min) | T½ (min) | Area Under Curve (ng min ml$^{-1}$) | Bioavailability (%) | Clearance *(ml min$^{-1}$ kg$^{-1}$) | Apparent Volume of Distribution *(lkg$^{-1}$) |
| --- | --- | --- | --- | --- | --- | --- | --- |
| IF | 121 | 15 | 51 | 9382 | 32.9 | 5.3 | 0.37 |
| JF | 165 | 10 | 41 | 10631 | 37.3 | 5.3 | 0.31 |
| KF | 110 | 15 | 42 | 7581 | 26.6 | 5.3 | 0.31 |
| Mean | 132 | 13 | 45 | 9198 | 32.3 | 5.3 | 0.33 |

*values corrected for bioavailable dose

EXAMPLE 2

A bioadhesive powder formulation of morphine-6-glucuronide was prepared using microspheres of cross-linked starch. The microspheres were prepared by the method described in GB 1518121 or EP 223302 described above. A preferred size of microspheres is 1–100 μm.

75 mg of morphine-6-glucuronide was dissolved in 30 ml water and mixed with 1 g of starch microspheres. The product was freeze-dried to produce a free flowing powder. The final concentration of morphine metabolite in the product was 0.075 mg/mg of starch microspheres.

The powder was administered to the nasal cavity using an insufflator device. The quantity administered was 2.0 mg microspheres per kg body weight containing 0.15 mg morphine-6-glucuronide.

EXAMPLE 3

A bioadhesive powder formulation of morphine-6-sulphate was prepared using microspheres of cross-linked starch. The microspheres were prepared by the method described in GB 1518121 or EP 223302 described above. A preferred size of microspheres is 1–100 μm.

75 mg of morphine-6-sulphate was dissolved in 30 ml water and mixed with 1 g of starch microspheres. The product was freeze-dried to produce a free flowing powder. The final concentration of morphine metabolite in the product was 0.075 mg/mg of starch microspheres.

The powder was administered to the nasal cavity using an insufflator device. The quantity administered was 2.0 mg microspheres per kg body weight containing 0.15 mg morphine-6-sulphate.

EXAMPLE 4

The bioadhesive microsphere system described in Examples 2 and 3 were prepared but in addition an absorption enhancing agent was employed. A preferred material is lysophosphatidyl glycerol (LPG). 100 mg LPG was added to the suspension of the morphine metabolite and microspheres. The freeze dried product was administered as a powder as in Example 1 and 2. The final quantities of morphine-6-glucuronide or morphine-6-sulphate and enhancing agent were 7.5 mg and 10 mg, respectively in a 100 mg dose of microspheres.

EXAMPLE 5

A liquid formulation similar to that described in Example 1 was prepared with added absorption enhancing agent as follows.

150 mg of morphine-6-glucuronide was dissolved in 10 ml of a 0.5% solution of medium viscosity grade of Chitosan (80% degree of deacetylation, Protan Limited). The substituted cyclodextrin material dimethyl-β-cyclodextrin (Sigma Chemical Comp) was added to provide a concentration of 5%. The liquid formulation was administered using a conventional pump spray device.

EXAMPLE 6

The formulation described in Example 5 was prepared but in the place of the dimethyl-β-cyclodextrin, α-cyclodextrin (Sigma Chemical Co.) at the same concentration of 50 mg/ml was added.

EXAMPLE 7

The microsphere formulation described in Example 4 was prepared but instead of the enhancing agent a chelating agent in the form of EDTA was employed. 50 mg of EDTA was added to the suspension of morphine metabolite and microspheres. The product was freeze dried as before in Example 2. The final quantities of morphine-6-glucuronide and chelating agent are 7.5 mg and 5 mg, respectively in a 100 mg dose of microspheres administered to sheep.

I claim:

1. A composition for nasal administration comprising a polar metabolite of an opioid analgesic selected from the group consisting of glucuronides and ethereal sulphates of an opioid analgesic, wherein the opioid analgesic is selected from the group consisting of morphine, codeine, levorphanol, hydromorphone, oxymorphone, nalbuphine, buprenophine, nalorphine, hydrocodone, oxycodone and butorphanol, and an effective amount of an absorption promoting agent to allow nasal absorption of a pharmacologically effective amount of the metabolite after nasal administration of the composition;

wherein the absorption promoting agent is selected from the group consisting of a cationic polymer, a surface active agent, a chelating agent, a mucolytic agent, a cyclodextrin, and combinations thereof.

2. A composition according to claim 1 wherein the metabolite is a glucuronide.

3. A composition according to claim 1 wherein the metabolite is an ethereal sulphate of an opioid analgesic.

4. A composition for nasal administration comprising morphine-6-glucuronide and an effective amount of an absorption promoting agent to allow nasal absorption of the morphine-6-glucuronide after nasal administration of the composition, wherein the absorption promoting agent is selected from the group consisting of a cationic polymer, a surface active agent, a chelating agent, a mucolytic agent, a cyclodextrin, and combinations thereof.

5. A composition for nasal administration comprising morphine-6-sulphate and an effective amount of an absorption promoting agent to allow nasal absorption of the morphine-6-sulphate after nasal administration of the composition, wherein the absorption promoting agent is selected from the group consisting of a cationic polymer, a surface active agent, a chelating agent, a mucolytic agent, a cyclodextrin, and combinations thereof.

6. The composition of claim 1 wherein the absorption promoting agent is a cationic polymer and wherein the cationic polymer is chitosan.

7. A composition according to claim 1 wherein the composition comprises a solution or dispersion of the absorption promoting agent.

8. A composition according to claim 1 wherein the composition comprises microspheres which are formed of an absorption promoting agent.

9. A method of delivery of a polar metabolite of an opioid analgesic comprising administering a composition for nasal administration to the nasal mucosa wherein the composition comprises a polar metabolite of an opioid analgesic selected from the group consisting of glucuronide and ethereal sulphates of an opioid analgesic, wherein the opioid analgesic is selected from the group consisting of morphine, codeine, levorphanol, hydromorphone, oxymorphone, nalbuphine, buprenorphine, nalorphine, hydrocodone, oxycodone and butorphanol, and an effective amount of an absorption promoting agent selected from the group consisting of a cationic polymer, a surface active agent, a chelating agent, a mucolytic agent, a cyclodextrin, and combinations thereof to allow nasal absorption of a pharmacologically effective amount of the metabolite.

10. A method of delivery of morphine-6-glucuronide comprising administering morphine-6-glucuronide and an effective amount of an absorption promoting agent to allow nasal absorption of the morphine-6-glucuronide after nasal administration of the composition, wherein the absorption promoting agent is selected from the group consisting of a cationic polymer, a surface active agent, a chelating agent, a mucolytic agent, a cyclodextrin, and combinations thereof.

11. A method of delivery of morphine-6-sulphate comprising administering a composition for nasal administration to the nasal mucosa wherein the composition comprises morphine-6-sulphate and an effective amount of an absorption promoting agent selected from the group consisting of a cationic polymer, a surface active agent, a chelating agent, a mucolytic agent, a cyclodextrin, and combinations thereof to allow nasal absorption of a pharmacologically effective amount of the morphine-6-sulphate.

12. The method of claim 11 wherein the absorption promoting agent is a cationic polymer which is chitosan, and wherein the chitosan is in the form of microspheres.

13. The method of claim 9 wherein the composition comprises a solution or dispersion of the absorption promoting agent.

14. The method of claim 9 wherein the composition comprises microspheres which are formed of an absorption promoting agent.

15. The composition of claim 1 wherein the polar metabolite is a morphine metabolite.

16. The composition of claim 1 wherein the absorption promoting agent is a surface active agent selected from the group consisting of a phospholipid and a lysophospholipid.

17. The method of claim 9 wherein the opioid analgesic is morphine.

18. The method of claim 9 wherein the absorption promoting agent is a surface active agent selected from the group consisting of a phospholipid and a lysophospholipid.

19. The method of claim 1 wherein the absorption promoting agent is a cationic polymer and wherein the cationic polymer is chitosan.

20. The method of claim 9 comprising nasally administering the composition in a pharmacologically effective amount for the alleviation of pain.

21. The composition of claim 1 wherein the absorption promoting agent is a surface active agent present in an amount between 0.02 and 10%.

22. The method of claim 9 wherein the absorption promoting agent is a surface active agent present in an amount between 0.02 and 10%.

* * * * *